United States Patent
Kuo et al.

(10) Patent No.: US 10,092,710 B2
(45) Date of Patent: Oct. 9, 2018

(54) METHOD OF OBTAINING A CLASSIFICATION BOUNDARY AND AUTOMATIC RECOGNITION METHOD AND SYSTEM USING THE SAME

(71) Applicant: National Yang-Ming University, Taipei (TW)

(72) Inventors: Wen-Chuan Kuo, Taipei (TW);
Chien-Kun Ting, Taipei (TW);
Meng-Chun Kao, Taipei (TW)

(73) Assignee: NATIONAL YANG-MING UNIVERSITY, Taipei (TW)

(*) Notice: Subject to any disclaimer, the term of this patent is extended or adjusted under 35 U.S.C. 154(b) by 98 days.

(21) Appl. No.: 15/204,478

(22) Filed: Jul. 7, 2016

(65) Prior Publication Data
US 2017/0007778 A1    Jan. 12, 2017

Related U.S. Application Data

(60) Provisional application No. 62/189,443, filed on Jul. 7, 2015.

(51) Int. Cl.
| | |
|---|---|
| G06K 9/00 | (2006.01) |
| A61M 5/46 | (2006.01) |
| A61B 5/00 | (2006.01) |
| G06T 11/00 | (2006.01) |
| A61B 1/313 | (2006.01) |
| G06T 7/12 | (2017.01) |
| G06T 7/143 | (2017.01) |

(52) U.S. Cl.
CPC ............ *A61M 5/46* (2013.01); *A61B 1/3135* (2013.01); *A61B 5/0066* (2013.01); *A61B 5/407* (2013.01); *A61B 5/6848* (2013.01); *G06T 7/12* (2017.01); *G06T 7/143* (2017.01); *G06T 11/003* (2013.01); *A61B 2505/05* (2013.01); *G06T 2207/10101* (2013.01); *G06T 2207/30088* (2013.01)

(58) Field of Classification Search
None
See application file for complete search history.

(56) References Cited

U.S. PATENT DOCUMENTS

2004/0093166 A1* 5/2004 Kil ........................ G01N 1/06
 702/19
2010/0298705 A1* 11/2010 Pelissier ............... A61B 8/0833
 600/443

OTHER PUBLICATIONS

Wen-Chuan Kua, et al; Fiber-Needle Swept-Source Opitcal Coherence Tomography System for the Indentification of the Epidural Space in Piglets; Anesthesiology, V 122, No. 3; Mar. 2015; 10 pgs.

* cited by examiner

*Primary Examiner* — Vikkram Bali
(74) *Attorney, Agent, or Firm* — Muncy, Geissler, Olds & Lowe, P.C.

(57) ABSTRACT

The present invention provides a method of obtaining a classification boundary, to limit an axial depth in a puncturing operation. The following steps of method comprises: At first, obtaining a plurality of tomographic images from the axial depth of a tissue is performed. Then, obtaining a plurality of characteristic values from the tomographic images, the characteristic values are classified by a Support Vector Machine method. A classification boundary will be obtained through a distribution of the graph for defining a specific compartment of the tissue. In addition, an automatic recognition method and system using the above mentioned method are also disclosed in the present invention.

8 Claims, 5 Drawing Sheets

METHOD OF OBTAINING A CLASSIFICATION BOUNDARY AND AUTOMATIC RECOGNITION METHOD AND SYSTEM USING THE SAME

RELATED APPLICATIONS

This Non-provisional application claims priority under 35 U.S.C. § 119(a) on Patent Application No. 62/189,443 filed in United States America [Jul. 7, 2015], the entire contents of which are hereby incorporated by reference.

FIELD OF THE INVENTION

The present disclosure relates to a method for obtaining a classification boundary. More particularly, the present disclosure relates to method for obtaining a classification boundary and an automatic recognition method and system for limiting an axial depth in a puncturing operation by classifying a plurality of characteristic values obtained from tomographic images of a tissue.

BACKGROUND

"Epidural anesthesia" is one of the most used treatments in regional anesthesia, such as epidural, lower-body operation and post-operative pain control. According to the estimation, the usage of the epidural anesthesia is around 10% of anesthesia now so that there are million cases per year in the world. Taking epidural as an example, there are around 40000 cases in Taiwan every year. For fat patients or the patients with structural spinal abnormalities, operating the epidural anesthesia will be harder as well as the requirements of a positioning needle will be also higher.

The anesthesia of the epidural space uses an epidural needle to penetrate through skin, muscle and ligamentum flavum (LF) for entering into the epidural space in the patient lower back or chest back. A catheter is placed inside and then anesthetics are injected for temporary blocking spinal nerve conduction to reduce the discomfort caused during surgery or post surgery. The epidural space is located between the ligamentum flavum and the dura mater and has a thickness around 2-7 mm. However, the epidural needle insertion is traditionally a blind technique whose success depends upon the experience of the operator. The failure rate of such an operation is around 1-3% and causes complications, such as acute headache.

In clinical, a method of loss of resistance, air or hanging-drop is performed in the epidural anesthesia for placing the epidural space catheter. That is, the operator will feel the loss of resistance after the needle tip goes through the ligamentum flavum for recognizing a position of the needle tip. When the needle penetrates through the ligamentum flavum of the patient, the needle, which is continuously pressed, will enter into the cavity due to the loss of the resistance of air or water for determining if the needle tip is located inside the epidural space. However, this method is not objective and depends on the experiences of operators.

Therefore, the palpation is still a main stream in the operation of the epidural anesthesia and depends on the experiences of the operator. Although pluralities of methods are provided in the prior art, several disadvantages are listed as the following table.

| Method | Disadvantages |
|---|---|
| High-frequency ultrasound transducer | 1. Ultrasound pulser/receiver has angle limit.<br>2. Resolution is not great. |
| Two-wavelength fiber-optics | 1. The epidural space distance[cannot be predicted.<br>2. There is no direct image. |
| Optical fibers for spectroscopy | 1. The epidural space distance[cannot be predicted.<br>2. There is no direct image. |
| Time-domain OCT | 1. There is no direct image. |

SUMMARY OF THE INVENTION

For improving the disadvantages of technology, the present invention provides a determining method of a classification boundary for limiting an axial depth in a puncture, includes the following steps.

At first, a) obtaining a plurality of tomographic images from the axial depth of a tissue, and b) a plurality of texture features of interesting are chosen from one of the tomographic images. Then, c) identifying color-scales of the texture features to obtain a plurality of characteristic values. d) The steps (b) to (c) will be repeated for obtaining the characteristic values from each of tomographic images of the tissue. Finally, e) showing the characteristic values in a graph by a classifying method, and obtaining a classification boundary through a distribution of the graph for defining a specific compartment of the tissue.

In an embodiment, the tissue is a compartment with a dura mater and a skin, and the specific compartment is a compartment of an epidural or a non-epidural when the puncture is an epidural puncture.

In other embodiment, the tomographic images are a plurality of optical tomographic images with an axially sector-shaped or an axially rectangle-shaped.

In other embodiment, the classifying method is Support Vector Machine method.

The present invention also provides an automatic recognition method for recognizing a real-time depth in a puncture whether reaches into a target axial depth, includes the following steps.

a) At first, obtaining a real time tomographic image from the axial depth of a tissue where a puncturing end is, and b) choosing a plurality of texture features of interesting from the real time tomographic image. Then, c) identifying color-scales of the texture features to obtain a plurality of characteristic values. d) A classifying method is utilized to show the characteristic values in a graph wherein the graph comprises the classification boundary obtained by the above determining method. Finally, e) determining whether the characteristic values locate inside a classification zone of the graph, if the characteristic values locate inside a zone I, the depth where puncturing end being is the target axial depth.

In an embodiment, the tissue is a compartment from a dura mater to a skin when the puncture is an epidural puncture.

In other embodiment, the real time tomographic images are a plurality of optical tomographic images with an axially sector-shaped or an axially rectangle-shaped.

In other embodiment, the classifying method is Support Vector Machine method.

Furthermore, the present invention provides an automatic recognition system for recognizing a real-time depth in a puncture. The system includes a puncturing end, an image capturing device, a feature analyzing device, a determining device and a monitor.

The image capturing device, which is connected to the puncturing end, is used to obtain a real time tomographic image from the axial depth of a tissue where a puncturing end is.

The feature analyzing device, which is connect with the optical image capturing device, is used to choose a plurality of texture features of interesting from the real time tomographic image and identifying color-scales of the texture features to obtain a plurality of characteristic values.

The determining device, which is connect with the feature analyzing device, is used to show the characteristic values in a graph by a classifying method wherein the graph comprises the classification boundary obtained by the above determining method, if the characteristic values locate inside a zone I, the depth where puncturing end being is the target axial depth.

The monitor, is used to display the real time tomographic image and a result from the determining device In an embodiment, the image capturing device is a swept-source optical coherence tomography or an optical coherence tomography using a broadband light source.

In other embodiment, the puncturing end includes an inner optical fiber probe connected with a circular rotary motor or a reflector connected with a swing motor for obtaining the real time tomographic image in an axially sector-shape or an axially rectangle-shape.

In other embodiment, the tissue is a compartment from a dura mater to a skin when the puncture is an epidural puncture.

In other embodiment, the classifying method is Support Vector Machine method.

The features and advantages of the present disclosure will be understood and illustrated in the following specification and FIGS. 1~5.

BRIEF DESCRIPTION OF THE DRAWINGS

The disclosure can be sufficient to understand by reading the following description of the embodiment, with reference made to the accompanying drawings as follows.

DETAILED DESCRIPTION

The present invention provides a determining method of a classification boundary for limiting an axial depth in a puncture and an automatic recognition method for recognizing a real-time depth in the puncture whether reaches into a target axial depth. It is understood that the method provides merely an example of the many different types of functional arrangements that may be employed to implement the operation of the various components of a puncturing needle, a computer system connected to the puncturing needle, a multiprocessor computing device, and so forth. The execution steps of the present invention may include application specific software which may store in any portion or component of the memory including, for example, random access memory (RAM), read-only memory (ROM), hard drive, solid-state drive, magneto optical (MO), IC chip, USB flash drive, memory card, optical disc such as compact disc (CD) or digital versatile disc (DVD), floppy disk, magnetic tape, or other memory components.

For example, the computer system comprises an input device, a storage medium, a memory, a processor and a display device. The input device is used to provide data such as image, text or control signals to a processer such as a computer or other information appliance. The storage medium such as, by way of example and without limitation, a hard drive, an optical device or a remote database server is coupled to a network, and stores software programs. The memory typically is space where information encoded, stored, and retrieved etc from the process. The processer performs data calculations, data comparisons, and data copying. The display device visually conveys text, graphics, and video information. Information shown on the display device is called soft copy because the information exists electronically and is displayed for a temporary period of time. The display device includes CRT monitors, LCD monitors and displays, gas plasma monitors, and televisions.

In an embodiment of the present invention, the software programs are stored in the memory and executed by the processor when the computer system executes the determining method or the automatic recognition method. Finally, information will be provided by the processor, and presented on the display device or stored in the storage medium.

Figure 1:
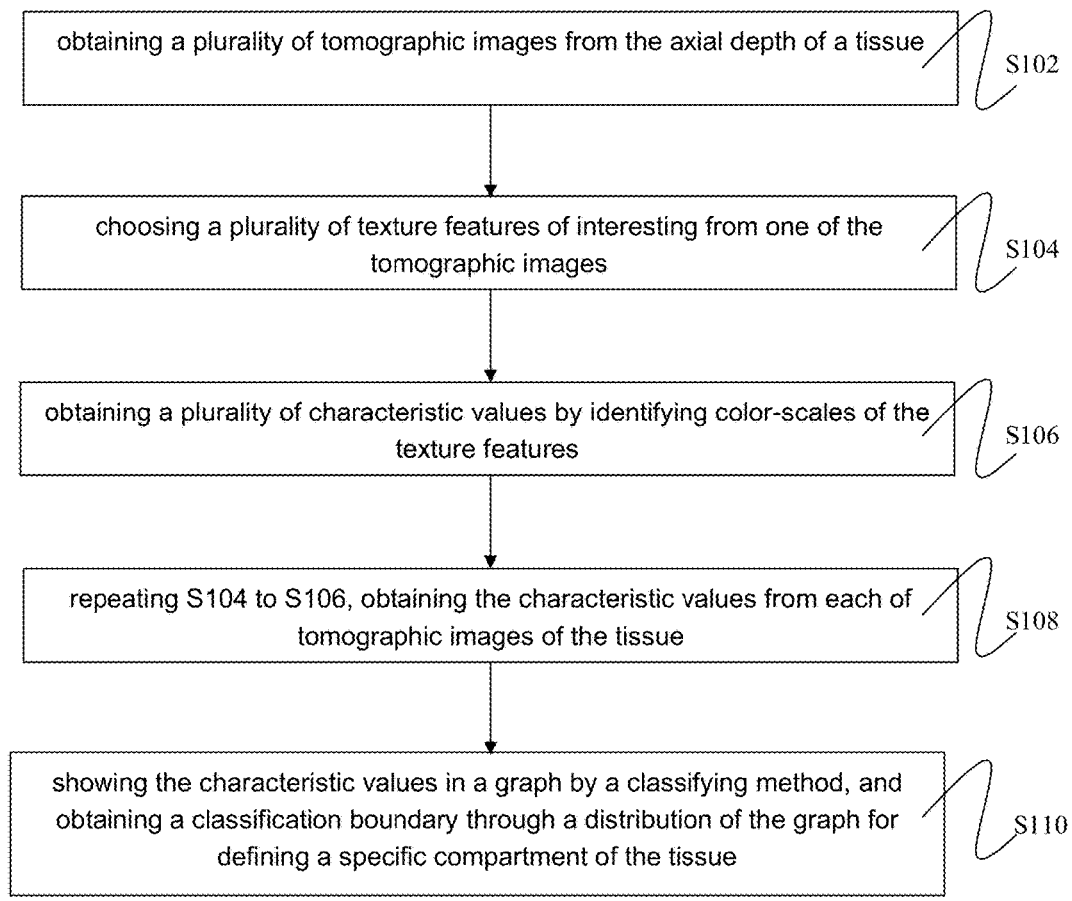
FIG. 1 is a flow chart showing a determining method of a classification boundary for limiting an axial depth in a puncture according to an embodiment of the present disclosure.

Please refer to FIG. 1, which is a flow chart showing a determining method of a classification boundary according to an embodiment of the present disclosure. As shown in the figure, the method comprises the following steps.

In Step S102, a plurality of tomographic images are obtained from an axial depth of a tissue as shown. The tissue can be a spinal cord which may include skin, muscle, ligamentum flavum and fat. In Step S104, a plurality of texture features are chosen from one of the tomographic images, and in Step S106, color-scales of the texture features are identified to obtain a plurality of characteristic values. In Step S108, the Step S104 to Step S106 will be repeated for obtaining the characteristic values from each of tomographic images of the tissue. The different tissues have different texture features and color levels. Therefore, in Step S110, the characteristic values are shown in a graph by a classifying method, and a classification boundary P is obtained through a distribution of the graph for defining a specific compartment of the tissue. Preferably, the classifying method is Support Vector Machine method but the present disclosure is not limited thereto.

Figure 2:
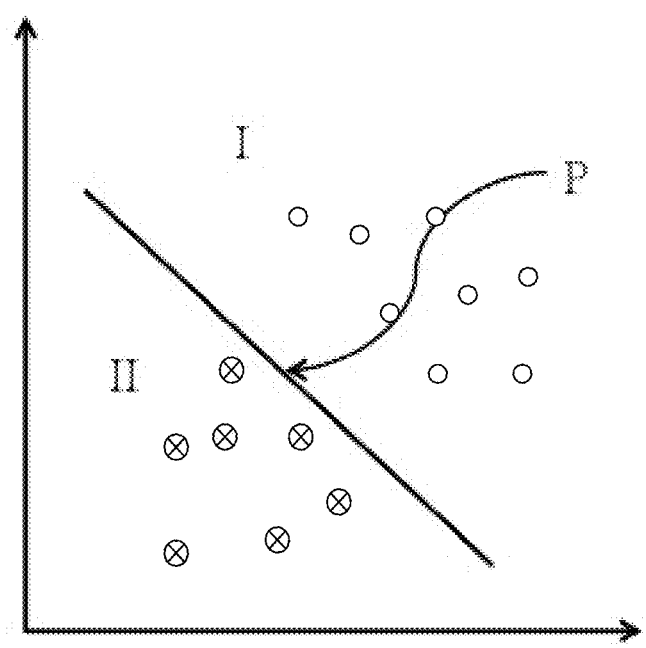
FIG. 2 is a schematic drawing showing a graph with a classification boundary according to the present disclosure.

Please refer to FIG. 2, which is a schematic drawing showing a graph with a classification boundary according to the present disclosure. The classification boundary P can divide the distribution of the graph into Zone II and I. In an embodiment of the present invention, the method is provided for limiting an axial depth in a puncture. Zone I represents the puncturing end located inside the spinal space, and Zone II represents the puncturing end located outside the spinal space. In particular, the tissue is a compartment with a dura mater and a skin, and the specific compartment is a compartment of an epidural or a non-epiduralt when the puncture is an epidural puncture. However, the present disclosure is not limited thereto.

The present disclosure further provides an automatic recognition method and system using the abovementioned classification boundary. The automatic recognition method is provided for recognizing a real-time depth in a puncture whether reaches into a target axial depth. The automatic recognition system is provided for recognizing a real-time depth in a puncture.

Figure 3:
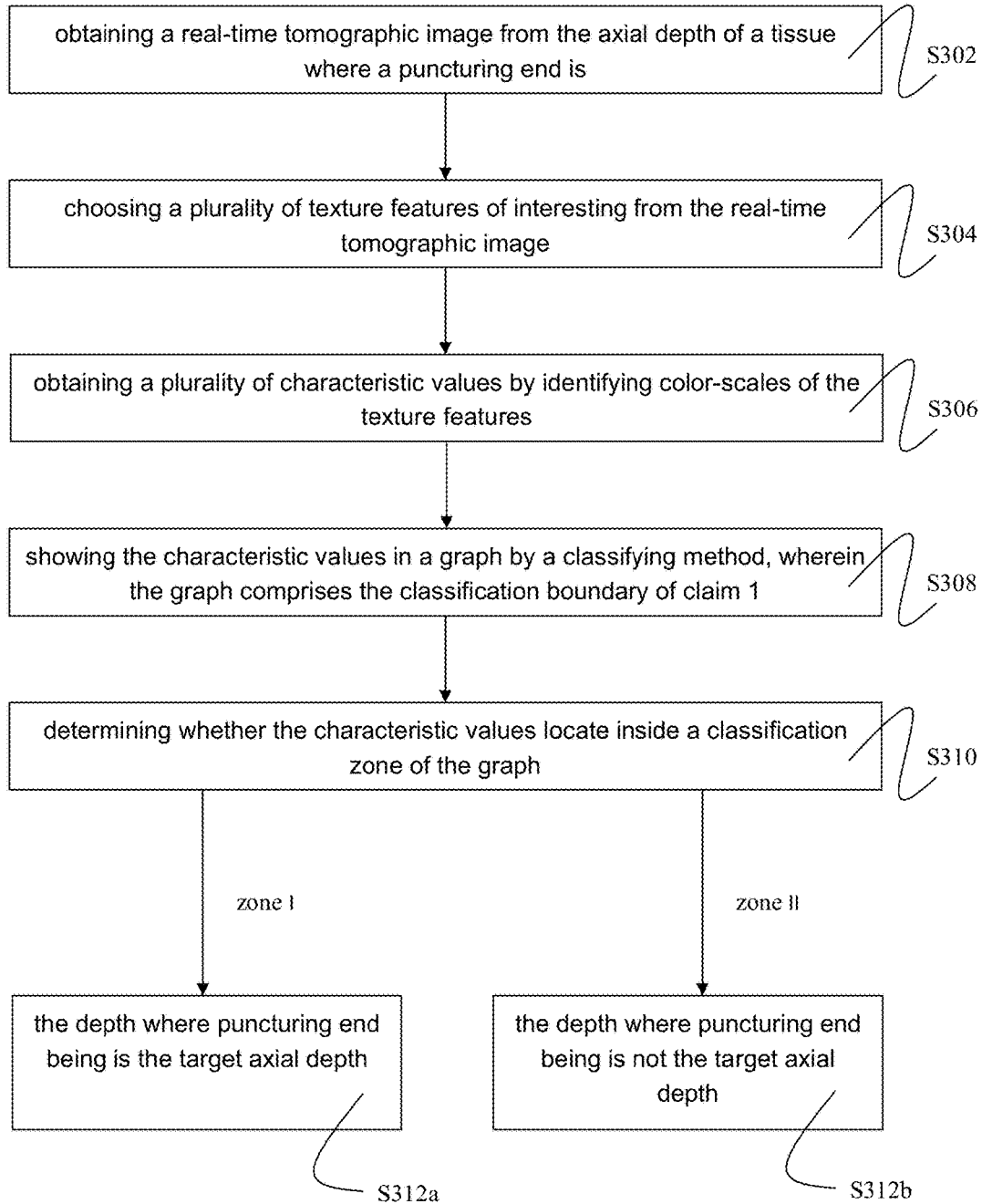
FIG. 3 is a flow chart showing an automatic recognition method for recognizing a real-time depth in a puncture whether reaches into a target axial depth according to an embodiment of the present disclosure.
Figure 4:
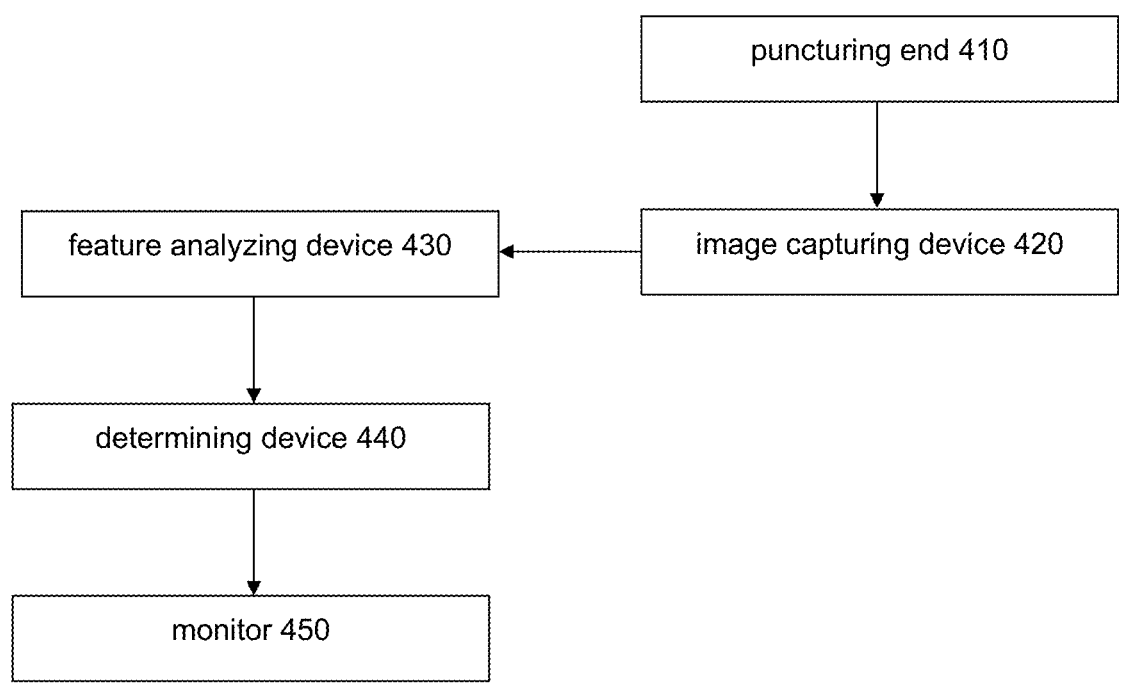
FIG. 4 is a schematic drawing showing an automatic recognition system for recognizing a real-time depth in a puncture according to an embodiment of the present disclosure.

Please refer to FIG. 3 and FIG. 4, which are a flow chart showing an automatic recognition method according to an embodiment of the present disclosure and a schematic drawing showing an automatic recognition system 100 according to an embodiment of the present disclosure, respectively. The automatic recognition system 400 includes an image capturing device 420, a feature analyzing device 430, a determining device 440 and a monitor 450.

The image capturing device 420, which is connected to a puncturing end 410, is used to obtain a real time tomographic image from the axial depth of a tissue where the puncturing end 410 is during the puncture as shown in Step S302.

Then, the feature analyzing device 430, which is connect with the optical image capturing device 420, is used to choose a plurality of texture features of interesting from the real-time tomographic image as shown in Step S304, and identifying color-scales of the texture features to obtain a plurality of real-time characteristic values as shown in Step S306.

It has different characteristic values between of different tissues. Therefore, the determining device 440 further shows the characteristic values in the graph comprises the classification boundary P by the classifying method as shown in Step S308. The classification boundary P is obtained by performing Steps S102~S110 and there is no further description herein.

In Step S310, the determining device 440 determines whether the characteristic values locate inside the classification zone of the graph, that is, Zone II or I of FIG. 2. If the real-time characteristic values locate inside the zone I, it is seen that the depth where puncturing end being is the target axial depth as shown in Step S312a. Otherwise, if the real-time characteristic values locate inside the zone II, the depth where puncturing end being is not the target axial depth as shown in Step S310b.

Finally, the monitor 450 is used to display the real time tomographic image and a result from the determining device.

In an embodiment of the present invention, the image capturing device 420 is an optical coherence tomography, which uses a swept-source laser or a broadband laser as a light source. The main output of the laser is coupled into a fiber-based Michelson interferometer and split into a reference optical source and a sample optical source. The sample optical source is pointed to the tissue, and the real time tomographic images are interference signals of a reflected light of the sample optical source and the reference optical source.

In other embodiment of the present invention, the puncturing end 410 is a puncture needle. In particular, the puncture needle includes a connecting cylinder and an outer sleeve tube, which is hollow and connected to the bottom of the connecting cylinder via its top. In some cases, the puncture needle can be any one of well-known epidural needles, such as an 18-gauge Tuohy needle. However, the present disclosure is not limited thereto.

Moreover, an inner optical fiber probe or a reflector is placed into the needle to form an endoscopic needle for proving the real-time image of the tissue by cooperating with the swept-source optical coherence tomography. It is noted that the inner optical fiber probe is connected to a circular rotary motor and the reflector is connected to a swing motor for obtaining the real time tomographic image of the tissue with an axially sector shaped or an axially rectangle-shaped.

To sum up, the present invention obtains the characteristic values of different tissues by analyzing the texture features and color-scales between each of tissues. Accordingly, the automatic recognition method can determine different real time tomographic images of the tissue for recognizing a real-time depth in a puncture. Moreover, the present invention utilizes the optical coherence tomography (OCT), which uses the swept-source or the broad-band source, to cooperate with the endoscopic needle having the circular rotary motor or the swing motor for obtaining the real time tomographic image of the tissue with the axially sector shaped or the axially rectangle-shaped as shown in FIGS. 5A and 5B.

Figures 5A, 5B:
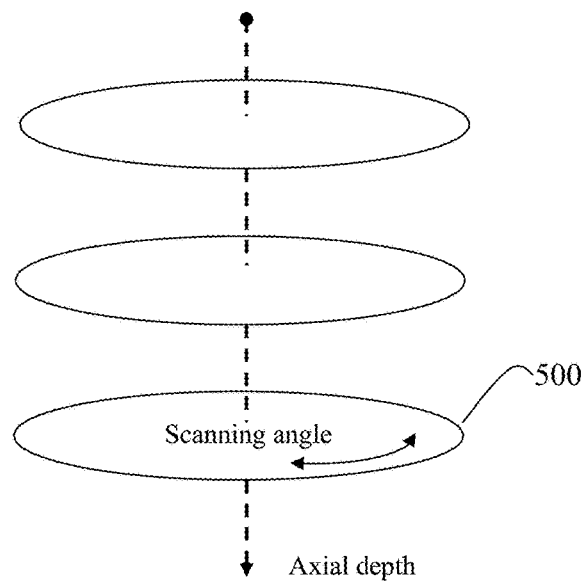
FIGS. 5A and 5B are the optical real time tomographic images in an axially sector-shape according to an embodiment of the present disclosure.

Please refer to FIG. 5B, which shows the optical real time tomographic images with the axially sector-shaped of different tissues, it can be divided into the zone I, which includes the ligamentum flavum and the epidural, and the zone II, which includes the muscle. The obtained images will be further processed for automatic recognition whether t a real-time depth of the puncture needle is inside the spinal space or not. Therefore, the safety of the puncture is ensured for dramatically reducing the risk of palpation.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A determining method of a classification boundary for limiting an axial depth in an epidural puncture, comprising:
   (a) obtaining a plurality of tomographic images from different axial depths of a tissue where a puncturing end is, wherein the tissue is a compartment between a dura mater and a skin;
   (b) choosing a plurality of texture features of interesting from one of the tomographic images;
   (c) obtaining a plurality of characteristic values by identifying intensity of the texture features in a correspondence color-scale;
   (d) repeating (b) to (c), obtaining the characteristic values from each of the tomographic images with the different axial depths;
   (e) mapping the characteristic values on a high dimensions' space, through Support Vector Machine method calculating a hyperplane which is best able to divide the congregation data of a first specific compartment and a second specific compartment on the high dimensions' space to distinguish different collections, and
   (f) defining a first specific compartment as a Zone I and a second specific compartment is opposite to the first specific compartment as a Zone II in the graph, wherein Zone I represents the characteristic values of the tomographic images from the puncturing end located inside the spinal space and Zone II represents the characteristic values of the tomographic images from the puncturing end located outside the spinal space; and (g) limiting the axial depth in the epidural puncture from the high dimensions' graph.

2. The method of claim 1, wherein the tomographic images are a plurality of optical tomographic images with an axially sector-shaped or an axially rectangle-shaped.

3. An automatic recognition method for recognizing a real-time depth in an epidural puncture whether reaches into a target axial depth, comprising:

(a) obtaining a real time tomographic image from a first axial depth of a tissue where a puncturing end is, wherein the tissue is a compartment between a dura mater and a skin;

(b) choosing a plurality of texture features of interesting from the real time tomographic image;

(c) obtaining a plurality of characteristic values by identifying intensity of the texture features in a correspondence color-scale;

(d) mapping the characteristic values on a high dimensions' space with a hyperplane as claim 1 through Support Vector Machine method; and (e) determining whether the characteristic values locate inside a Zone I or a Zone II of the high dimensions' graph, wherein Zone I represents the puncturing end located inside the spinal space, and Zone II represents the puncturing end located outside the spinal space;

(f) if the characteristic values located inside the Zone I, the first axial depth where puncturing end being is the target axial depth, otherwise obtaining the real time tomographic image from a second axial depth of the tissue and repeating step a) to e).

4. The method of claim 3, wherein the real time tomographic images are a plurality of optical tomographic images with an axially sector-shaped or an axially rectangle-shaped.

5. An automatic recognition system for recognizing a real-time depth in an epidural puncture, comprising:

an image capturing device, which is connected to a puncturing end, is used to obtain a real time tomographic image from a first axial depth of a tissue where a puncturing end is, wherein the tissue is a compartment between a dura mater and a skin; and a multiprocessor computing device, comprising:

a feature analyzing processor, which is connected with the image capturing device, is used to choose a plurality of texture features of interesting from the real time tomographic image, and identifying intensity of the texture features in a correspondence color-scale to obtain a plurality of characteristic values;

a determining processor, which is connected with the feature analyzing processor, is used to map the characteristic values on a high dimensions' space with a hyperplane as claim 1 through Support Vector Machine method;

mean, in the determining processor, for determining whether the characteristic values locate inside a Zone I or a Zone II of the high dimensions' space, wherein Zone I represents the puncturing end located inside the spinal space, and Zone II represents the puncturing end located outside the spinal space, if the characteristic values locate inside the Zone I, the first axial depth where puncturing end being is the target axial depth as the result, otherwise requiring the real time tomographic image from a second axial depth of the tissues as the result, and a monitor, is used to display the real time tomographic image and a result from the determining processor.

6. The system of claim 5, wherein the image capturing device is a swept-source optical coherence tomography or an optical coherence tomography using a broadband light source.

7. The system of claim 5, wherein the puncturing end includes an inner optical fiber probe connecting with a circular rotary motor.

8. The system of claim 5, wherein the puncturing end includes a reflector connected with a swing motor.

\* \* \* \* \*